(12) United States Patent
Choi et al.

(10) Patent No.: US 11,013,228 B2
(45) Date of Patent: May 25, 2021

(54) METHOD OF PROCESSING ALLOGRAFT SKIN FOR TRANSPLANTATION, AND CRYOPRESERVED ALLOGRAFT SKIN PRODUCED THEREBY

(75) Inventors: Weon Ik Choi, Seongnam (KR); Wook Chun, Seoul (KR); Jae Deuk Jung, Seoul (KR)

(73) Assignee: CG BIO CO., LTD.

( * ) Notice: Subject to any disclaimer, the term of this patent is extended or adjusted under 35 U.S.C. 154(b) by 359 days.

(21) Appl. No.: 13/386,111

(22) PCT Filed: Jun. 11, 2010

(86) PCT No.: PCT/KR2010/003782
§ 371 (c)(1),
(2), (4) Date: Jan. 20, 2012

(87) PCT Pub. No.: WO2011/010796
PCT Pub. Date: Jan. 27, 2011

(65) Prior Publication Data
US 2012/0122071 A1    May 17, 2012

(30) Foreign Application Priority Data
Jul. 22, 2009   (KR) .................. 10-2009-0066925

(51) Int. Cl.
*A01N 1/02* (2006.01)
*A61L 27/60* (2006.01)
*A61L 27/36* (2006.01)

(52) U.S. Cl.
CPC .......... *A01N 1/0221* (2013.01); *A61L 27/362* (2013.01); *A61L 27/60* (2013.01); *A61L 2430/40* (2013.01)

(58) Field of Classification Search
None
See application file for complete search history.

(56) References Cited

U.S. PATENT DOCUMENTS 6,492,103 B1 * 12/2002 Taylor ................. A01N 1/02
                                                                435/1.2
6,740,484 B1 *  5/2004 Khirabadi et al. ............. 435/1.3
(Continued)

FOREIGN PATENT DOCUMENTS

KR   10-1999-0014353 A    2/1999
KR   10-2002-0086678 A   11/2002
(Continued)

OTHER PUBLICATIONS

Applegate et al, Whole-Cell Bioprocessing of Human Fetal Cells for Tissue Engineering of Skin, Feb. 4, 2009, Skin Pharmacol Physiol 22:63-73.*

(Continued)

*Primary Examiner* — Sharmila G Landau
*Assistant Examiner* — Stephanie A McNeil
(74) *Attorney, Agent, or Firm* — Fennemore Craig. P.C.

(57) ABSTRACT

The present invention relates to a method of processing allograft skin for transplantation and a cryopreserved allograft skin produced thereby. More specifically, the present invention relates to a method in which a cryoprotectant is prepared by adding sucrose to basic constituents comprising dimethyl sulfoxide, an animal cell culture medium and fetal bovine serum, and then the resulting solution is used to subject skin tissue for transplantation to a freezing process.

5 Claims, 3 Drawing Sheets

(56) References Cited

U.S. PATENT DOCUMENTS

| | | | |
|---|---|---|---|
| 2004/0067480 A1* | 4/2004 | Brockbank | A01N 1/02 435/1.1 |
| 2004/0209235 A1 | 10/2004 | Goldstein et al. | |
| 2006/0210960 A1* | 9/2006 | Livesey | A01N 1/00 435/2 |
| 2009/0029340 A1* | 1/2009 | Gabbai | A01N 1/02 435/1.3 |

FOREIGN PATENT DOCUMENTS

| | | |
|---|---|---|
| KR | 10-2006-0099312 A | 9/2006 |
| KR | 10-2008-0068897 A | 7/2008 |

OTHER PUBLICATIONS

Muller-Schweinitzer et al, Sucrose promotes the functional activity of blood vessels after cryopreservation in DMSO-containing fetal calf serum, Jan. 6, 1992, Naunyn-Schmiedeberg's Arch Pharmacol 345 : 594-597.*

McCarthy et al, Cutaneous innervation in sensory neuropathies: Evaluation by skin biopsy, 1995, Neurology, 45: 1848-1855.*

Isachenko et al, Ultrarapid Freezing of Rat Embryos with Rapid Dilution of Permeable Cryoprotectants, Cryobiology 34, 157-164 (1997).*

Wang et al, The Cryopreservation of a Tissue Engineered Dermal Replacement by Programmed Freezing , 2005, Proceedings of the 2005 IEEE Engineering in Medicine and Biology 27th Annual Conference, pp. 494-497.*

PCT/KR2010/003782 International Search Report, dated Jan. 5, 2011, 2 pages.

* cited by examiner

METHOD OF PROCESSING ALLOGRAFT SKIN FOR TRANSPLANTATION, AND CRYOPRESERVED ALLOGRAFT SKIN PRODUCED THEREBY

TECHNICAL FIELD

The present invention relates to a method of processing allograft skin for transplantation and a cryopreserved allograft skin produced thereby. More specifically, the present invention relates to a method in which a cryoprotectant is prepared by adding sucrose to basic constituents comprising dimethyl sulfoxide, an animal cell culture medium and fetal bovine serum, and then the resulting solution is used to subject skin tissue for transplantation to a freezing process.

BACKGROUND ART

Skin is the largest organ, covering the entire human body, and has functions of preventing loss of body fluid, influx of toxic substances and microbes from the external, and protecting the body from physical and chemical stimuli. In the case of a patient whose skin is seriously impaired by severe burns, injury, carcinoma excision, skin diseases and the like, a protective membrane is needed to prevent infection of impaired regions and the loss of body fluid, along with not leaving a scar at the impaired region and preventing serious shrinkage accompanied by the process of spontaneous cure. For regenerating impaired skin tissue, there are three methods of autograft in which a patient's own skin is transplanted, allograft in which the skin of another human being is transplanted and xenograft in which the skin of an animal is transplanted. Among them, autograft is the most ideal. However, when burnt areas are extensive, there is a limitation in the region from which skin tissue may be obtained, and the harvesting region can leave a new scar. Allograft plays a greater role in helping the movement of cells at the periphery of the impaired region and curing than permanent engraftment.

Specifically, in the case of a third-degree burn in which epidermis, dermis and subcutaneous layers are impaired, skin grafting is essentially required. At present, autograft is most often used as skin grafting. However, harvesting autograft tissue creates a new injury, increasing patient's pain, time for complete recovery can be extended, and the economic burden is greater. In addition, when insufficient healthy regions remain—as with a severely burned patient—autograft cannot be applied or grafting operations should be performed repeatedly. To resolve the above problems, allograft using the skin of another person and xenograft using the skin of an animal such as a pig have been tried. However, other side effects as well as immunorejection often result.

In the case of burn surgeries which are most generally performed in domestic and foreign hospitals, the dead epidermis and dermis layers are removed and skin grafting is then carried out by using an acellular dermis in which the epidermis and cells in the dermis are removed from skin harvested from a corpse to avoid immunorejection. Cultured keratinocytes will then complete the entire skin thereon. Because such a completed skin includes basement membrane, it can play a role in protecting the body from external hazardous substances. However, such a skin graft is very expensive and has a problem in balancing supply and demand since most skin grafts are imported.

In addition, the conventional method for processing skin harvested from a donor is a glycerol preservation in which skin is treated with sequential concentrations of glycerol. However, the above method has a problem wherein treatment duration is long since cell viability is low.

DETAILED DESCRIPTION OF THE INVENTION

Technical Problem

Therefore, the technical problem to be solved in the present invention is the provision of a new method of processing allograft skin for transplantation which can efficiently increase cell viability and minimize change of biological properties compared with the conventional glycerol preservation method.

Solution to the Problem

To solve the above problems, the present invention provides a method of processing allograft skin for transplantation comprising:
 i) mixing fetal bovine serum, an animal cell culture medium and dimethyl sulfoxide;
 ii) dissolving sucrose in the solution to obtain a cryoprotectant;
 iii) penetrating the cryoprotectant into a separated skin; and
 iv) freezing the cryoprotectant-penetrated skin in a controlled rate freezer.

The present invention also provides a cryopreserved allograft skin which is processed by the above method.

Hereinafter, the present invention is described in detail.

In the present invention, dimethyl sulfoxide, an animal cell culture medium and fetal bovine serum are used as basic constituents of a cryoprotectant. In the present invention, dimethyl sulfoxide, the animal cell culture medium and fetal bovine serum may be preferably used in a mixing ratio of 1:3~5:4~6 based on weight. If the mixing ratio of the animal cell culture medium is less than 3, the cell death rate may be increased due to the lack of essential nutrients. If the mixing ratio of the animal cell culture medium is greater than 5, the cell death rate may be increased due to freezing damage. If the mixing ratio of fetal bovine serum is less than 4, there may be a problem of freezing damage due to the lack of plasma proteins which protect skin tissue from freezing damage. If the mixing ratio of fetal bovine serum is greater than 6, there may be a problem of cell activity due to excessive plasma ingredients. In the present invention, the mixing ratio of dimethyl sulfoxide, the animal cell culture medium and fetal bovine serum is most preferably 1:4:5 based on weight. In the present invention, the example of the animal cell culture medium includes, but is not limited to, MEM, DMEM, RPMI 1640, IMDM, Defined Keratinocyte-SFN (without BPE), Keratinocyte-SFN (with BPE), Knock-Out D-MEM, AmnioMAX-II Complete Medium, AmnioMAX-C100 Complete Medium.

In the present invention, a cryoprotectant is prepared by dissolving sucrose in a solution in which the above basic constituents are mixed. In the present invention, when sucrose is added to the cryoprotectant, it plays a role in stabilizing and protecting cell membranes and cell membrane proteins from ice crystals formed at a freezing step. As a result, the cryopreserved allograft skin prepared according to the method of the present invention can show improved cell viability. In addition, the optimal mixing ratio of sucrose, fetal bovine serum and dimethyl sulfoxide improves cell viability. In the present invention, sucrose is preferably dissolved in the basic constituents-mixed solution as 25 to 40 wt % in the final concentration. If the concentration of sucrose is less than 25 wt %, the effects of sucrose to protect and stabilize cell membranes and cell membrane proteins needed to improve cell viability may be insufficient. If the concentration of sucrose is greater than 40 wt %, cell death rate may be increased due to high concentration of sugar ingredients. In the present invention, the cryoprotectant is most preferably prepared by dissolving sucrose in the basic constituents-mixed solution as 30 wt % in the final concentration.

In the present invention, the penetration of the cryoprotectant into skin tissue may be carried out according to conventional methods known in the art. Preferably, the cryoprotectant may be penetrated into the skin tissue in a low temperature bath. Time needed for penetration may vary depending on the size of skin tissue and other factors. For example, the cryoprotectant may be penetrated into the skin tissue in a 4° C. low temperature bath for about 6-24 hours.

In the present invention, the cryoprotectant-penetrated skin is frozen by using a controlled rate freezer. Use of the controlled rate freezer allows the skin tissue to be frozen at a desired rate. In the present invention, the freezing rate of skin with the controlled rate freezer is preferably −0.1° C. to −7° C. per minute, most preferably −1° C. per minute. When the skin tissue is frozen, the temperature of cryoprotectant-penetrated skin is different from the chamber temperature of the controlled rate freezer. As a result, if latent heat of fusion is not controlled by an excessive freezing rate of 10° C. per minute due to rapid freezing from the region in which latent heat of fusion is generated at freezing to −80° C. which is the temperature where the movement of water molecules stops, the skin tissue may be damaged by the formation of ice crystals.

Effects of the Invention

The cryopreserved allograft skin prepared according to the present invention shows increased cell viability and minimum change of biological properties. As a result, the success rate of acellular dermis grafting can be increased, and treatment duration can be curtailed by helping to regenerate granulation tissue at the transplanted region.

DESCRIPTION OF EMBODIMENTS

The present invention is explained in more detail with the following examples. However, it must be understood that the protection scope of the present invention is not limited to the examples.

Because human skin tissue harvested from a donor (cadaver) is prohibited from being used in an experiment, pig skin—which is the closest to human skin—is used for preparing ten (10) of both cryopreserved skins and glycerol-preserved skins according to the following methods of Example and Comparative Example.

EXAMPLE

Cryopreserved skin was prepared with pig skin according to the following steps.
(1) Pig skin was washed with saline solution.
(2) The pig skin was cut at the size of 5×10 cm$^2$.
(3) Dimethyl sulfoxide (Sigma, USA), DMEM (Gibco, USA) and fetal bovine serum (Gibco, USA) were mixed in the weight ratio of 1:4:5.
(4) Sucrose was added to the solution of step (3) as the final concentration of 30 wt % and dissolved to obtain a cryoprotectant.
(5) The pig skin of step (2) was immersed in the cryoprotectant of step (4).
(6) A low temperature bath (P-039, CoreTech, Korea) was set at 4° C.
(7) The pig skin of step (5) was put in the 4° C. low temperature bath, and then the cryoprotectant was penetrated into the pig skin for 12 hours.
(8) The penetration-completed pig skin and 50 ml of the cryoprotectant were put in a polyamide bag (CryoBag™, Origen, USA).
(9) A controlled rate freezer was prepared.
(10) The polyamide bag of step (8) was put in the controlled rate freezer and frozen to −150° C. with the rate of −1° C. per minute.
(11) After freezing, the polyamide bag was kept frozen in a dry shipper until analysis experiments.

Comparative Example

A glycerol-preserved skin was prepared with pig skin by sequentially treating it with 50% glycerol and 85% glycerol according to the following steps.
(1) Pig skin was washed with saline solution.
(2) The pig skin was cut at the size of 5×10 cm2.
(3) The pig skin was immersed in 50% glycerol diluted with distilled water for 72 hours.
(4) The pig skin of step (3) was immersed in 85% glycerol for 72 hours.

Experimental Example 1

Figure 1:
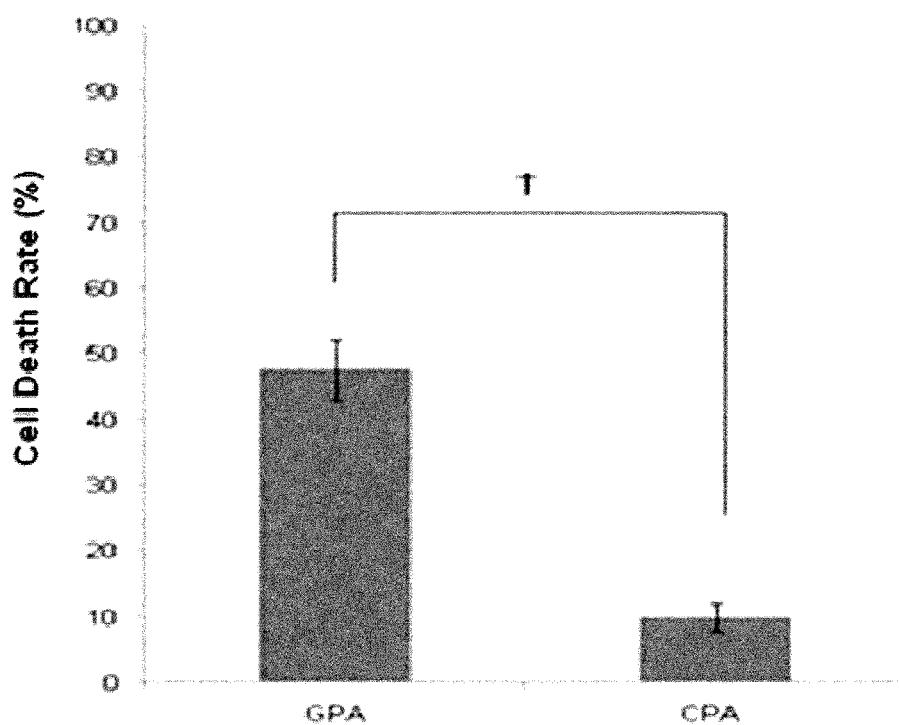
FIG. 1 is a graph representing the cell death rate of glycerol-preserved allograft (GPA) and cryopreserved allograft (CPA) measured by TUNEL assay.
Figure 2:
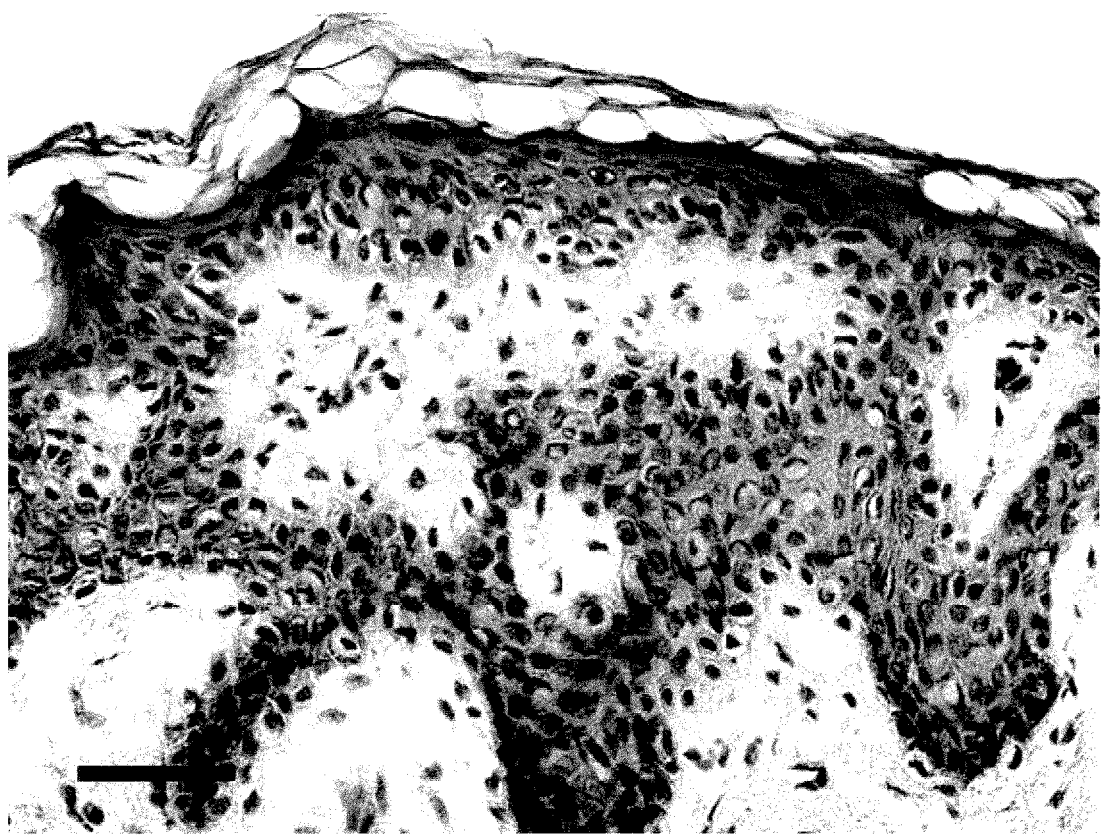
FIG. 2 is an optical microscope photograph of glycerol-preserved allograft after H&E staining (200 times magnification)
Figure 3:
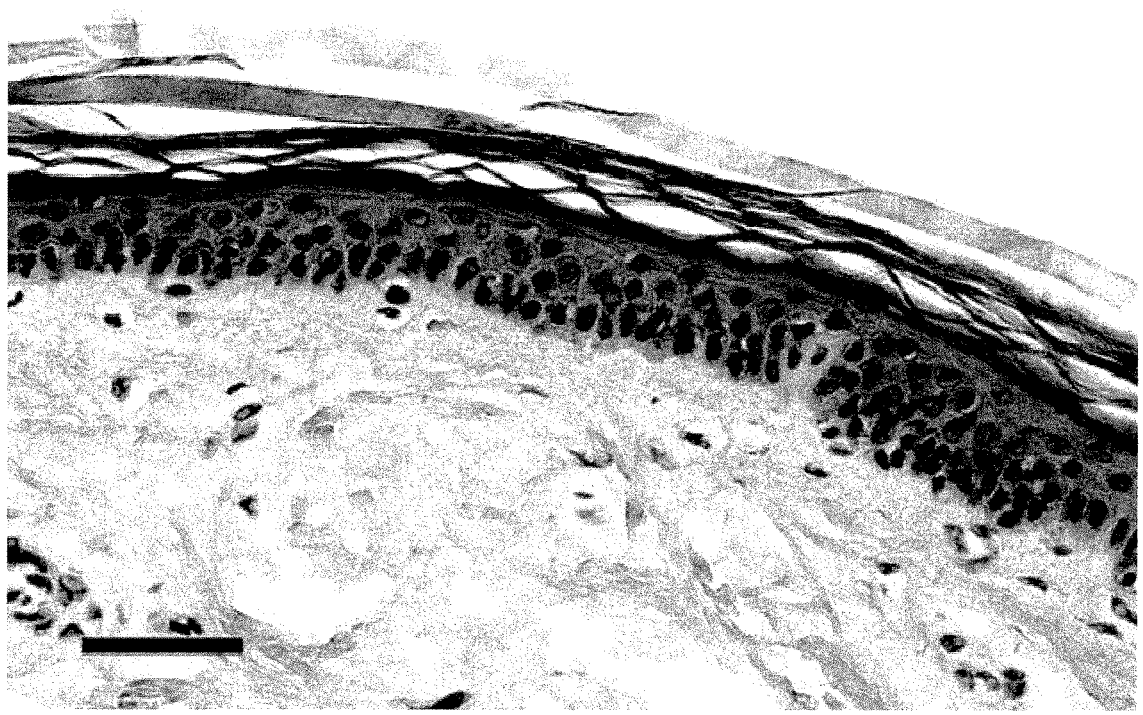
FIG. 3 is an optical microscope photograph of cryopreserved allograft after H&E staining (200 times magnification).
Figure 4:
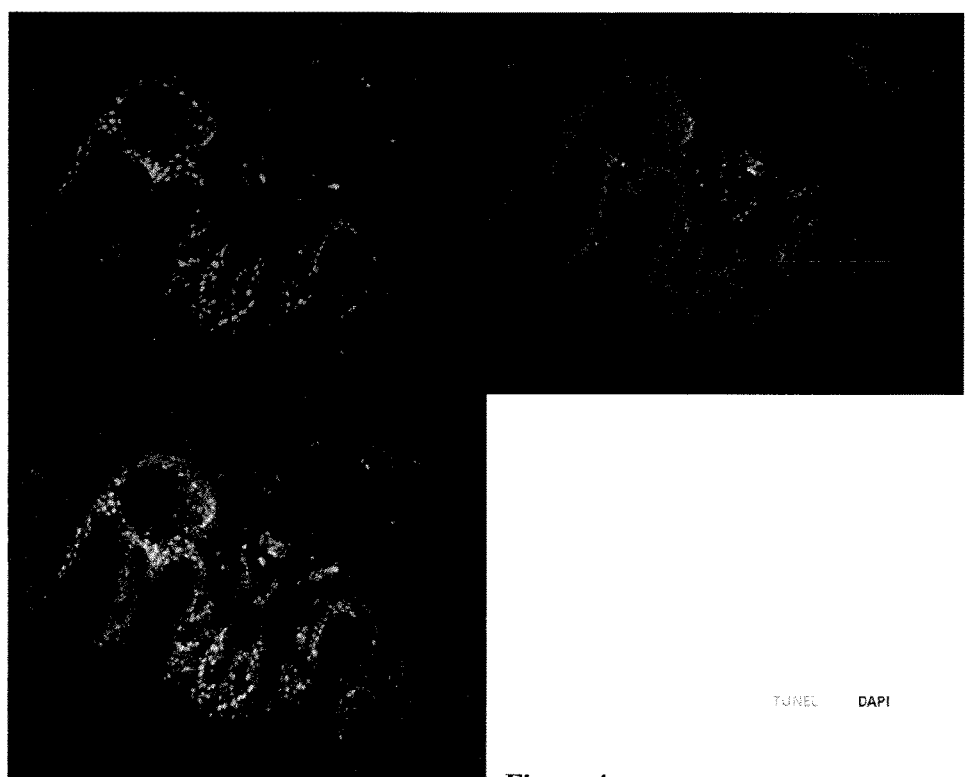
FIG. 4 is a fluorescence microscope photograph of glycerol-preserved allograft after TUNEL staining (100 times magnification)
Figure 5:
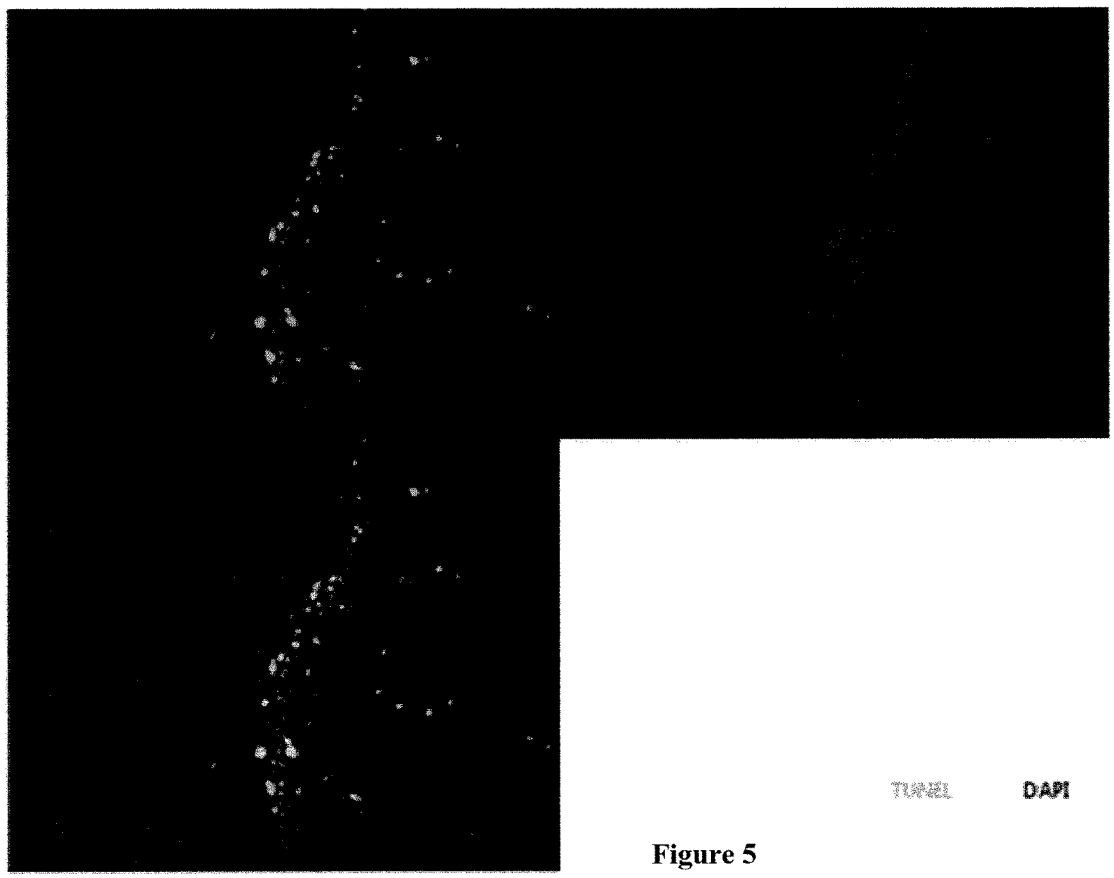
FIG. 5 is a fluorescence microscope photograph of cryopreserved allograft after TUNEL staining (100 times magnification).

The pig skins prepared according to the above Example and Comparative Example were analyzed by TUNEL (terminal deoxynucleotidyl transferase dUTP nick end labeling) assay. TUNEL assay was carried out by using an In Situ Cell Death Detection Kit, Fluorescein (Roche, Germany) according to the manufacturer's instructions. The results of the cell death rate are represented in FIG. 1. (The results are a mean of 10 samples.)

Pictures of the skins of the Example and Comparative Example were taken with a microscope (Olympus BX51), and the results are shown in FIGS. 2, 3, 4 and 5.

As can be seen from FIG. 1, the cell death rate in the Example is 4-5 times lower than that of the Comparative Example.

In addition, from the microscope photographs of FIGS. 2, 3, 4 and 5, it can be seen that cell death in the skin tissue in the Example is clearly smaller than that in the Comparative Example.

That is, the method according to the present invention shows higher cell viability compared with the conventional glycerol preservation method. As a result, the cryopreserved allograft skin according to the present invention can increase the success rate of acellular dermis grafting and curtail the treatment duration by helping to regenerate granulation tissue at the transplanted region.

Experimental Example 2

To investigate the change of the cell death rate according to the difference of sucrose concentration, the cryopreserved allograft skin was prepared by the same method as in the Example except that the sucrose concentration in the cryoprotectant was 5, 10, 15, 20, 25, 30, 35 and 40 wt %, and it was then analyzed by TUNEL assay. TUNEL assay was carried out by using an In Situ Cell Death Detection Kit, Fluorescein (Roche, Germany) according to the manufacturer's instructions, and 4',6-diamidino-2-phenylindole (DAPI) was used as a fluorescent marker. The results of cell death rate are shown in the following Table 1, and represented in FIG. 6 as a graph.

TABLE 1

| n | Sucrose Conc. | | | | | | | |
|---|---|---|---|---|---|---|---|---|
| | 5 wt % | 10 wt % | 15 wt % | 20 wt % | 25 wt % | 30 wt % | 35 wt % | 40 wt % |
| 1 | 45 | 49 | 31 | 35 | 23 | 20 | 25 | 36 |
| 2 | 36 | 55 | 22 | 21 | 28 | 23 | 10 | 33 |
| 3 | 64 | 57 | 47 | 22 | 64 | 39 | 23 | 41 |
| 4 | 39 | 56 | 57 | 23 | 12 | 11 | 28 | 26 |
| 5 | 41 | 41 | 66 | 68 | 20 | 5 | 21 | 20 |
| 6 | 65 | 26 | 25 | 43 | 19 | 20 | 30 | 13 |
| AVE | 48 | 47 | 41 | 35 | 28 | 20 | 23 | 28 |
| SD | 13 | 12 | 18 | 18 | 19 | 12 | 7 | 10 |
| SE | 5.251455 | 4.91709 | 7.378648 | 7.441625 | 7.574812 | 4.744588 | 2.891559 | 4.284987 |

(Unit of cell death rate: %)

Figure 6:
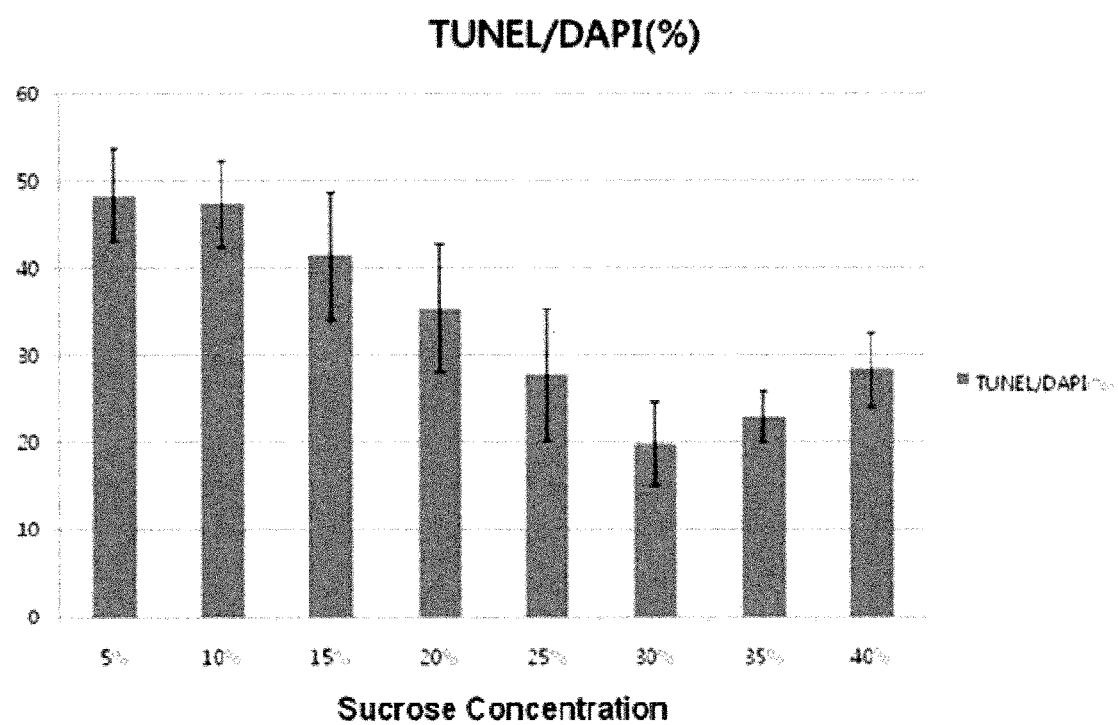
FIG. 6 is a graph representing the change of the cell death rate according to the sucrose concentration measured by TUNEL assay.

As can be seen from Table 1 and FIG. 6, when sucrose is comprised as 25 to 40 wt % in the final concentration, the cell death rate is quite low.

The invention claimed is:

1. A method of processing allograft of viable skin for transplantation comprising:
i) mixing a cryoprotectant solution to include dimethyl sulfoxide, sucrose, an animal cell culture medium and fetal bovine serum to obtain a cryoprotectant solution in which the mixing ratio of dimethyl sulfoxide, the animal cell culture medium and fetal bovine serum is 1:3-5:4-6 based on weight, and the sucrose has a final concentration of 25% to 40% by weight of the cryoprotectant solution;

ii) penetrating the cryoprotectant solution into a separated allograft of viable living skin for 6 to 24 hours; and iii) freezing the cryoprotectant-penetrated skin in a controlled rate freezer at a freezing rate of from −0.1 to −7° C. per minute.

2. The method of processing allograft skin for transplantation according to claim 1, wherein the final concentration of sucrose in the cryoprotectant solution is 30% by weight.

3. The method of processing allograft skin for transplantation according to claim 1, wherein the animal cell culture medium is selected from the group consisting of MEM, DMEM, RPMI 1640 and IMDM.

4. The method of processing allograft skin for transplantation according to claim 1, wherein the cryoprotectant is penetrated into the separated skin in a 4° C. low temperature bath for 6-24 hours.

5. The method of processing allograft skin for transplantation according to claim 1, wherein the cryoprotectant-penetrated skin is frozen in a controlled rate freezer with a freezing rate of −1° C. per minute.

\* \* \* \* \*